United States Patent
Gabay et al.

(10) Patent No.: US 11,419,612 B2
(45) Date of Patent: Aug. 23, 2022

(54) STABILIZING WIRES FOR MEDICAL DEVICE

(71) Applicant: St. Jude Medical, Cardiology Division, Inc., St. Paul, MN (US)

(72) Inventors: Gregory Gabay, New Hope, MN (US); Kristen T. Morin, St. Paul, MN (US); Andrey Samaray, Champlin, MN (US); Trevor Springer, Stillwater, MN (US)

(73) Assignee: St. Jude Medical, Cardiology Division, inc., St. Paul, MN (US)

( * ) Notice: Subject to any disclaimer, the term of this patent is extended or adjusted under 35 U.S.C. 154(b) by 99 days.

(21) Appl. No.: 17/097,179

(22) Filed: Nov. 13, 2020

(65) Prior Publication Data

US 2021/0145448 A1    May 20, 2021

Related U.S. Application Data

(60) Provisional application No. 62/935,897, filed on Nov. 15, 2019.

(51) Int. Cl.
*A61B 17/12* (2006.01)
*A61B 17/00* (2006.01)

(52) U.S. Cl.
CPC .......... *A61B 17/12168* (2013.01); *A61B 2017/00867* (2013.01); *A61B 2017/1205* (2013.01)

(58) Field of Classification Search
CPC ........ A61B 17/12031; A61B 17/12113; A61B 17/12099; A61B 17/12036; A61B 17/0057; A61B 17/12177; A61B 17/1204; A61B 17/12045; A61B 17/12145; A61B 17/12172; A61B 17/12168; A61B 17/1214; A61B 2017/1205; A61B 2017/00867; A61B 2017/00526; A61B 2017/00557; A61B 2017/00862; A61B 2017/12054; A61B 2017/00575; A61B 2017/00623; A61B 2017/00632
USPC ......................................................... 606/151
See application file for complete search history.

(56) References Cited

U.S. PATENT DOCUMENTS

| | | | |
|---|---|---|---|
| 2015/0133989 A1* | 5/2015 | Lubock ............ | A61B 17/12109 606/200 |
| 2018/0116678 A1* | 5/2018 | Melanson ........ | A61B 17/12131 |
| 2019/0274668 A1* | 9/2019 | Glimsdale ........ | A61B 17/12172 |

* cited by examiner

*Primary Examiner* — Katherine M Shi
*Assistant Examiner* — Paige A Codrington
(74) *Attorney, Agent, or Firm* — Armstrong Teasdale LLP (57) ABSTRACT

A medical device including stabilizing wires that are selectively movable from a first and second position and a delivery system including the same are described herein. The medical device includes a device body and the stabilizing wires coupled thereto. Each stabilizing wire has a proximal and distal end. In the first position, at least a portion of the distal end extends radially outwardly from the device body, and in the second position, the distal end is retracted within the device body. Each stabilizing wire includes a linear portion at the proximal end, a hook portion at the distal end, and a ramp segment extending between the linear portion and the hook portion, including a ramp incline portion that extends at a first angle from the linear portion to a ramp apex, and a ramp decline portion that extends at a second angle from the hook portion to the ramp apex.

20 Claims, 7 Drawing Sheets

FIG. 7

STABILIZING WIRES FOR MEDICAL DEVICE

CROSS-REFERENCE TO RELATED APPLICATIONS

The present application claims the benefit of priority to U.S. Provisional Patent Application No. 62/935,897, filed Nov. 15, 2019, the entire contents of which are hereby incorporated by reference in their entirety.

BACKGROUND OF THE DISCLOSURE

A. Field of Disclosure

The present disclosure relates generally to medical devices that are used in the human body. In particular, the present disclosure is directed to stabilizing wires incorporated into medical devices that are delivered to a target site within the human body using a delivery sheath. More specifically, the present disclosure is directed to stabilizing wires that would allow for recapture of the medical device while reducing a risk of delamination of the delivery sheath. Methods of using a delivery system to recapture such a medical device are also disclosed.

B. Background

A wide variety of medical devices are used to treat any target site, such as an abnormality, a vessel, an organ, an opening, a chamber, a channel, a hole, a cavity, or the like, located anywhere in the body. At least some medical devices include stabilizing wires that extend from a body of the medical device. The presence of stabilizing wires may decrease the risk of the medical device migrating from its deployed location over time.

However, once these medical devices with stabilizing wires are deployed, recapture may be difficult. Specifically, the stabilizing wires may scrape against an interior surface of the delivery sheath resulting in delamination of the delivery sheath, which may risk particulate creation. Accordingly, if a physician must recapture the device, a new delivery sheath must be used to re-deploy the device to the target site.

In addition, significant recapture force may be required to recapture these medical devices.

Accordingly, it would be desirable to incorporate stabilizing wires on medical devices while allowing for full recapture of the devices without the risk of delamination of the delivery sheath and creation of particulate matter. Additionally, it would be desirable to decrease the recapture force, allowing for an overall increase in the safety and efficiency of the procedure.

SUMMARY OF THE DISCLOSURE

In one embodiment, the present disclosure is directed to a medical device for treating a target site. The medical device includes a device body including at least one lobe formed from a shape memory material, and a plurality of stabilizing wires coupled to the device body. Each stabilizing wire has a respective proximal end and distal end and being selectively movable between a first position in which at least a portion of the distal end extends radially outwardly from the device body and a second position in which the distal end is retracted within the device body. Each stabilizing wire respectively includes a linear portion at least partially defining the proximal end, a hook portion at least partially defining the distal end, and a ramp segment extending between the linear portion and the hook portion. The ramp segment includes a ramp incline portion that extends at a first angle away from the linear portion to a ramp apex, and a ramp decline portion that extends at a second angle from the hook portion to the ramp apex.

In another embodiment, the present disclosure is directed to a delivery system including a medical device and a delivery sheath. The medical device includes a device body including at least one lobe formed from a shape memory material, and a plurality of stabilizing wires coupled to the device body. Each stabilizing wire has a respective proximal end and distal end and being selectively movable between a first position in which at least a portion of the distal end extends radially outwardly from the device body and a second position in which the distal end is retracted within the device body. Each stabilizing wire respectively includes a linear portion at least partially defining the proximal end, a hook portion at least partially defining the distal end, and a ramp segment extending between the linear portion and the hook portion. The ramp segment includes a ramp incline portion that extends at a first angle away from the linear portion to a ramp apex, and a ramp decline portion that extends at a second angle from the hook portion to the ramp apex. The delivery sheath is configured to retain and recapture the medical device during deployment of the medical device to a target site.

In a further embodiment, the present disclosure is directed to a method for recapturing a medical device. The method includes deploying a medical device at a target site using a delivery sheath, the medical device including a device body and a plurality of stabilizing wires coupled to the device body, each stabilizing wire having a respective proximal end and distal end and being selectively movable between a first position in which at least a portion of the distal end extends radially outwardly from the device body and a second position in which the distal end is retracted within the device body, each stabilizing wire respectively including: (i) a linear portion at least partially defining the proximal end, (ii) a hook portion at least partially defining the distal end, and (iii) a ramp segment extending between the linear portion and the hook portion, the ramp segment including a ramp incline portion that extends at a first angle away from the linear portion to a ramp apex, and a ramp decline portion that extends at a second angle from the hook portion to the ramp apex. The method also includes recapturing the medical device by: (a) advancing a distal end of the delivery sheath against a proximal end of the medical device, (b) further advancing the delivery sheath to engage the ramp portion of the stabilizing wires with the distal end of the delivery sheath and to transition the stabilizing wires from the first position to the second position, and (c) retracting the medical device into the delivery sheath.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings. It is understood that that Figures are not necessarily to scale.

DETAILED DESCRIPTION OF THE DISCLOSURE

The present disclosure generally relates to stabilizing wires incorporated into medical devices that are delivered to the target site by a delivery sheath. The present disclosure discloses medical devices having stabilizing wires including a ramped portion, which enables retraction of the stabilizing wires during recapture of the medical device. Accordingly, the medical devices of the present disclosure enable full recapture of the medical devices while reducing the risk of delamination of the delivery sheath, particulate formation from such delamination, and an overall reduction in recapture force.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

It is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as an LAA, an atrial septal defect, a lesion, a vessel dissection, or a tumor. Embodiments of the medical device may be useful, for example, for occluding an LAA, ASD, VSD, or PDA, as noted above. Furthermore, the term "lumen" is also not meant to be limiting, as the vascular abnormality may reside in a variety of locations within the vasculature, such as a vessel, an artery, a vein, a passageway, an organ, a cavity, or the like. As used herein, the term "proximal" refers to a part of the medical device or the delivery device that is closest to the operator, and the term "distal" refers to a part of the medical device or the delivery device that is farther from the operator at any given time as the medical device is being delivered through the delivery device.

The medical device may include one or more layers of occlusive material, wherein each layer may be comprised of any material that is configured to substantially preclude or occlude the flow of blood so as to facilitate thrombosis. As used herein, "substantially preclude or occlude flow" shall mean, functionally, that blood flow may occur for a short time, but that the body's clotting mechanism or protein or other body deposits on the occlusive material results in occlusion or flow stoppage after this initial time period.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

Figure 1:
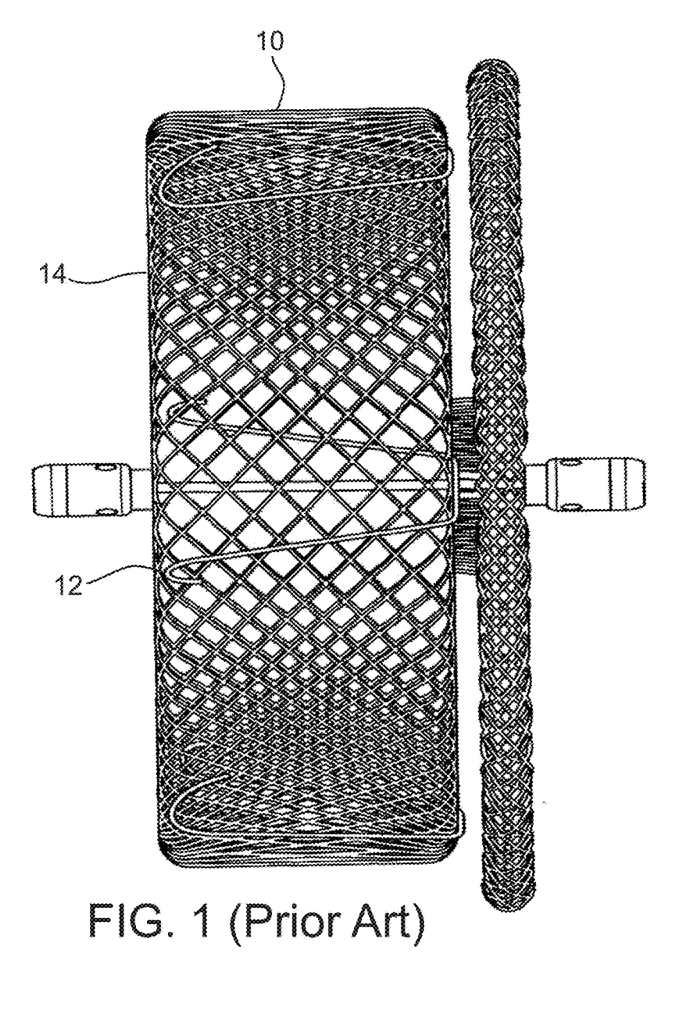
FIG. 1 illustrates a known medical device including at least one stabilizing wire.

In at least some conventional or known medical devices, such as a medical device 10 shown in FIG. 1, stabilizing wires 12 extend from a device body 14 of medical device 10. These stabilizing wires 12 are configured to retain medical device 10 at a desired target site within a human body, and prevent medical device 10 from being dislodged from the target site after deployment of medical device 10. However, stabilizing wires 12 are substantially straight from a proximal end to a distal end thereof. As described above, when such medical devices 10 are recaptured, stabilizing wires 12 interfere with such recapture. In particular, a recapture force is relatively high, and, moreover, stabilizing wires 12 scrape and delaminate an inner surface of a delivery sheath (not shown in FIG. 1), which risks particulate formation. Accordingly, where medical device 10 has been recaptured, the delaminated delivery sheath must be withdrawn from the target site and replaced.

The medical devices of the present disclosure, which include ramped stabilizing wires, avoid at least these disadvantages of known medical devices.

Figure 2:
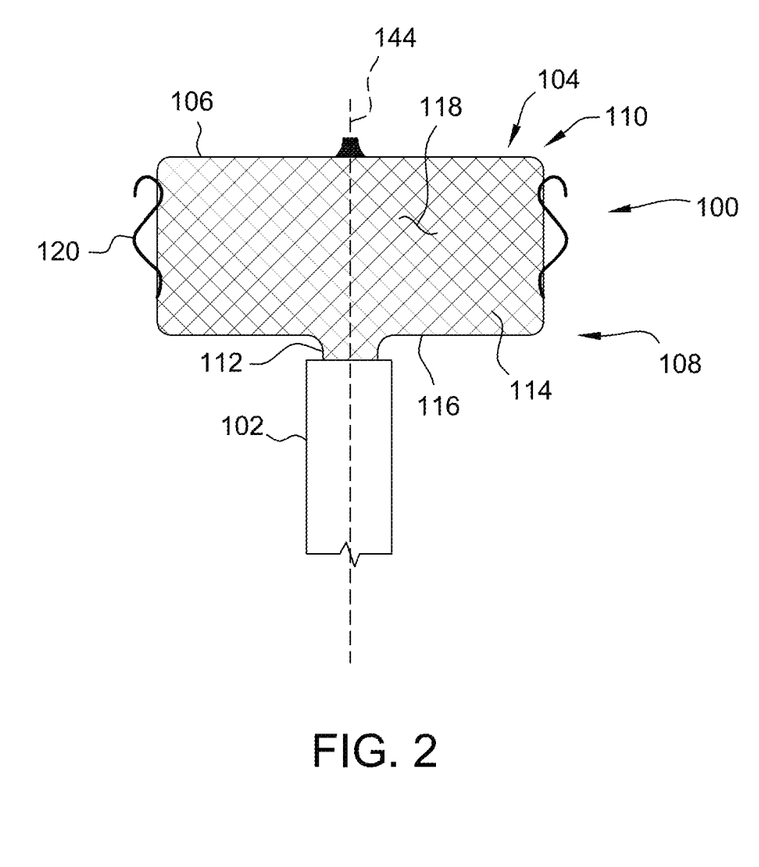
FIG. 2 is an exemplary embodiment of a delivery system including a delivery sheath and a medical device including stabilizing wires in accordance with the present disclosure.

Turning now to FIG. 2, a schematic diagram of a delivery system 100 is shown. Delivery system 100 includes a delivery sheath 102 that is configured to retain and recapture a medical device 104 during deployment of medical device 104 to a target site. Medical device 104 is deployed to treat a target site, and includes a device body 106 having a proximal end 108 and a distal end 110. Proximal end 108 is coupled to a delivery cable 112, which enables deployment of medical device 104 to the target site by advancing medical device 104 distally through delivery sheath 102 and, in accordance with the present disclosure, to recapture medical device 104 by at least partially retracting medical device 104 proximally into delivery sheath 102.

In the exemplary embodiment, device body 106 includes at least one lobe 114, which includes an exterior surface 116 that defines a cavity 118 within the at least one lobe 114.

In one embodiment, medical device 104 (e.g., device body 106) is formed from a shape-memory material, and may include a plurality of strands having a braided mesh configuration. One particular shape memory alloy that may be used is Nitinol. Nitinol alloys are also highly elastic and are said to be "superelastic," or "pseudoelastic." This elasticity may allow the device to return to a preset expanded configuration for deployment following passage in a distorted form through a delivery catheter. Further examples of materials and manufacturing methods for medical devices with shape memory properties are provided in U.S. Publication No. 2007/0265656 titled "Multi-layer Braided Structures for Occluding Vascular Defects" and filed on Jun. 21, 2007, which is incorporated by reference herein in its entirety.

As shown in FIG. 2, medical device 104 further includes a plurality of stabilizing wires 120 in accordance with the present disclosure. Stabilizing wires 120 have the configuration shown in FIG. 2 and illustrated in further detail in FIG. 3, which reduce a recapture force require to recapture medical device 104 within delivery sheath 102, and which reduce or eliminate delamination of delivery sheath during recapture. Stabilizing wires 120 are coupled to lobe 114 and are selectively movable between a first position in which at least a portion of stabilizing wires 120 extend radially outwardly from lobe 114 and a second position in which at least a portion of stabilizing wires 120 are retracted within lobe 114.

In some embodiments of the present disclosure, medical device 104 may be back-loaded into delivery sheath 102 (e.g., by a physician, before a medical procedure is initiated), such that medical device 104 is loaded into delivery sheath 102 in a reverse direction of its deployment. Back-loading medical device 104 enables the physician to attach a single delivery cable (e.g., delivery cable 112) to medical device 104 a single time, as medical device 104 is pulled into delivery sheath 102 "backwards" and then, during deployment of medical device 104, to push medical device 104 forward with the same delivery cable.

Figure 3:
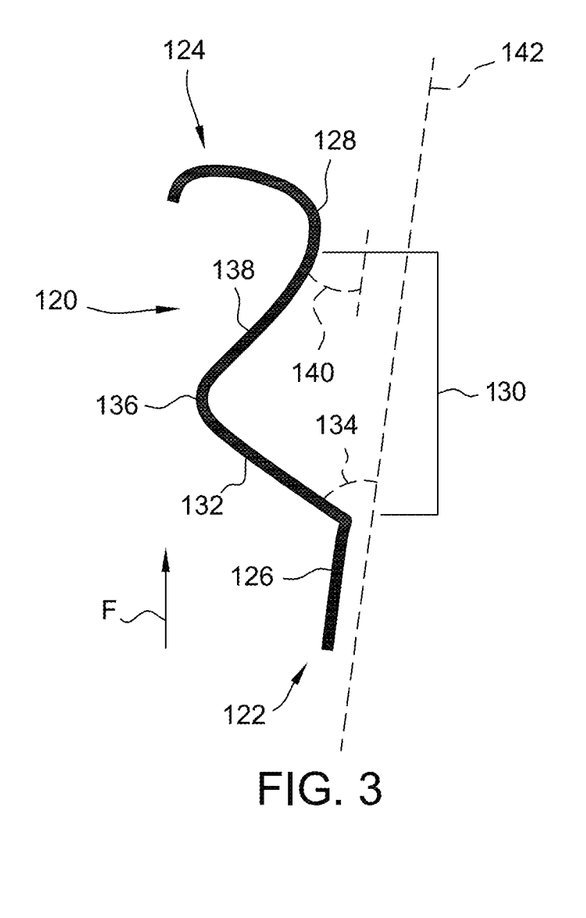
FIG. 3 illustrates the stabilizing wires in accordance with the present disclosure.

FIG. 3 illustrates one of stabilizing wires 120 in greater detail. Stabilizing wire 120 includes a proximal end 122 and a distal end 124. A linear portion 126 of stabilizing wire 120 at least partially defines proximal end 122, and a hook portion 128 at least partially defines distal end 124. Linear portion 126 is linear or straight, and hook portion 128 is generally U-shaped.

A ramp segment 130 extends between linear portion 126 and hook portion 128. Ramp segment 130 includes a first portion 132, also referred to as a ramp incline portion, that extends at a first angle 134 from linear portion 126 to a ramp apex 136, and a second portion 138, also referred to as a ramp decline portion, that extends at a second angle 140 from hook portion 128 to ramp apex 136. In some embodiments, first angle 134 may be an angle between about 30° and about 90°, or about 60° to about 80°. Second angle 140 may be an angle between about 30° and about 90°, or about 60° to about 80°.

Ramp incline portion 132 may be understood to extend away from linear portion 126 towards ramp apex 136, and/or towards linear portion 126 from ramp apex 136. Ramp incline portion 132 may be further understood to extend radially outwardly—from linear portion 126 to ramp apex 136—with respect to a theoretical axis 142 defined parallel to linear portion 126. Additionally or alternatively, ramp incline portion 132 may be understood to extend generally radially outward, with respect to a central axis 144 (see FIG. 2) of medical device 104, from linear portion 126 to ramp apex 136.

Conversely, ramp decline portion 138 may be understood to extend towards hook portion 128 from ramp apex 136, and/or away from hook portion 128 towards ramp apex 136. Ramp decline portion 138 may be further understood to extend radially inwardly—from ramp apex 136 to hook portion 128—with respect to theoretical axis 142. Additionally or alternatively, ramp decline portion 138 may be understood to extend generally radially inward, with respect to central axis 144, from ramp apex 136 to hook portion 128.

In the exemplary embodiment, ramp apex 136 is a curved or arcuate transition between ramp incline portion 132 and ramp decline portion 138. In such embodiments, ramp apex 136 enables further reduction of the recapture force of medical device 104 by facilitating smooth engagement between delivery sheath 102 and medical device 104, as described further herein. Alternatively, ramp apex 136 is an angular or otherwise shaped transition.

In the exemplary embodiment, stabilizing wires 120 are coupled to device body 106 (e.g., to lobe 114) at respective proximal ends 122 thereof. For example, each stabilizing wire 120 may be welded, sutured/sewn, or otherwise coupled to device body 106. Moreover, stabilizing wires 120 are coupled to device body 106 such that proximal ends 122 are positioned proximate to proximal end 108 of device body 106, and distal ends 124 are positioned proximate to distal end 110 of device body 106. In some embodiments, as shown in FIG. 2, stabilizing wires 120 are positioned at least partially external to exterior surface 116 of device body 106.

Stabilizing wires 120 are transitioned from the first position to the second position by exerting a force on ramp incline portion 132 in a distal direction, as generally indicated by arrow F in FIG. 3, as described further herein. Because of the angle of ramp incline portion 132 (e.g., first angle 134), such an upward force F is decomposed into both an upward component and an inward component (e.g., towards central axis 144). The inward component of the force F causes stabilizing wires 120 to be urged inwardly (e.g., towards central axis 144), and to rotate or pivot about proximal ends 122, which in turn causes distal ends 124 to be rotated inwardly with respect to device body 106. More specifically, distal ends 124, including hook portions 128, are retracted into cavity 118 of lobe 114 (e.g., inwardly past exterior surface 116). In the second position, at least a portion of distal ends 124 (e.g., at least a portion of hook portions 128) are retracted into cavity 118. In some embodiments, an entirety of distal ends 124 are retracted into cavity 118 in the second position. That is, hook portions 128 are entirely positioned within cavity 118. Accordingly, hook portions 128 do not interfere with recapture of medical device 104, and delamination of delivery sheath 102 is prevented.

Turning now to FIGS. 4A-4D, recapture of a deployed medical device 104 using delivery system 100 is shown. As used herein, "deployment" of medical device 104 may refer to an initial deployment of medical device 104 at or near a target site, and does not necessarily include a final placement of medical device 104.

In the exemplary embodiment, interaction between delivery sheath 102 and ramp segments 130 activates the transition of stabilizing wires 120 from the first position to the second position. Once stabilizing wires 120 have reached the second position, delivery sheath 102 may fully recapture medical device 104 without delamination of an interior surface of delivery sheath 102.

Figure 4A:
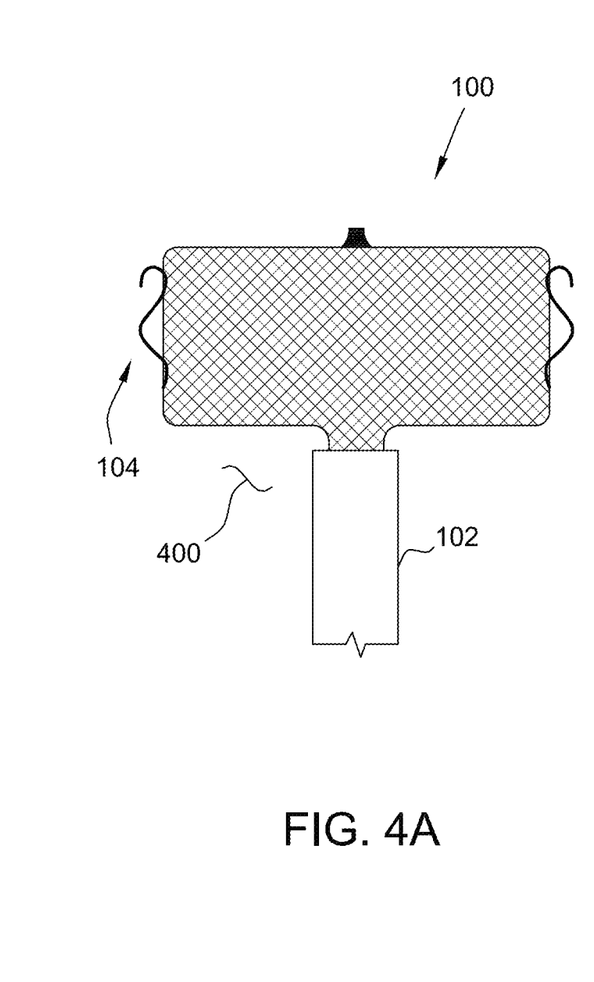
FIGS. 4A-4D depict a method of recapturing the medical device using the delivery sheath as shown in FIG. 2, specifically illustrating retraction of the stabilizing wires into the medical device as the delivery sheath is advanced.
Figures 4B, 4C:
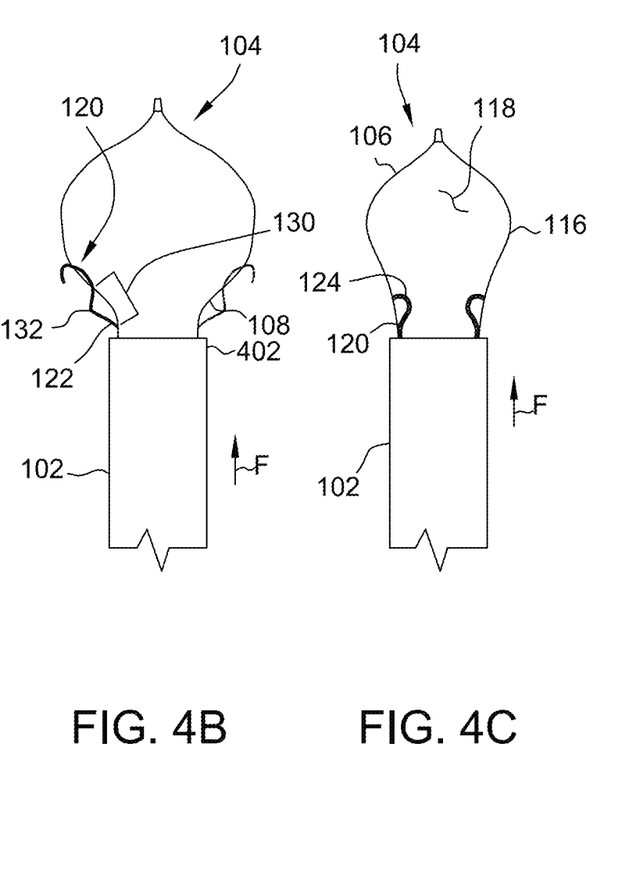

FIG. 4A illustrates medical device 104 in an initially deployed position at a target site 400. An operator of delivery system 100 (e.g., a physician) may determine that the deployed position of medical device 104 is incorrect or undesirable, and may therefore wish to recapture and reposition medical device 104 at target site 400. Accordingly, as illustrated in FIG. 4B, medical device 104 is proximally retracted into delivery sheath 102. This relative movement of medical device 104 and delivery sheath 102 may also be described as advancing delivery sheath 102 distally, relative to medical device 104. Such relative language will be used further herein, but it should be understood that in operation, medical device 104 is retracted into delivery sheath 102 during recapture thereof.

Figure 4D:
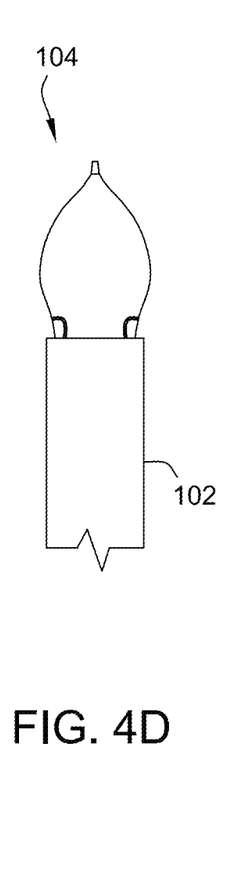

In particular, in FIG. 4B, a distal end 402 of delivery sheath 102 is advanced towards proximal end 108 of medical device 104. As delivery sheath 102 is advanced, distal end 402 of delivery sheath 102 engages proximal ends 122 of stabilizing wires 120. Subsequently, as delivery sheath 102 is further advanced, distal end 402 thereof contacts or engages with ramp segment 130. Specifically, delivery sheath 102 exerts an upward force (e.g., force F, shown in FIG. 3) against ramp incline portion 132, to initiate the transition of stabilizing wires from the first position (as shown in FIG. 4A) to the second position (as shown in FIGS. 4C and 4D).

As shown in FIG. 4C, as delivery sheath 102 continues to advance distally, force F on ramp incline portion 132 causes stabilizing wires 120 to rotate inwardly (e.g., towards central axis 144), into the second position. Once distal end 402 of delivery sheath 102 has reached ramp apex 136, stabilizing wires 120 are considered to be in the second position, in which distal ends 124 thereof are retracted into device body 106 (e.g., within cavity 118). Medical device 104 may then be fully retracted into delivery sheath 102, as shown in FIG. 4D, to enable full recapture thereof without delamination of delivery sheath 102 and with reduced recapture forces (compared to, for example, partial or full recapture of the medical device 10 shown in FIG. 1).

Figure 5A:
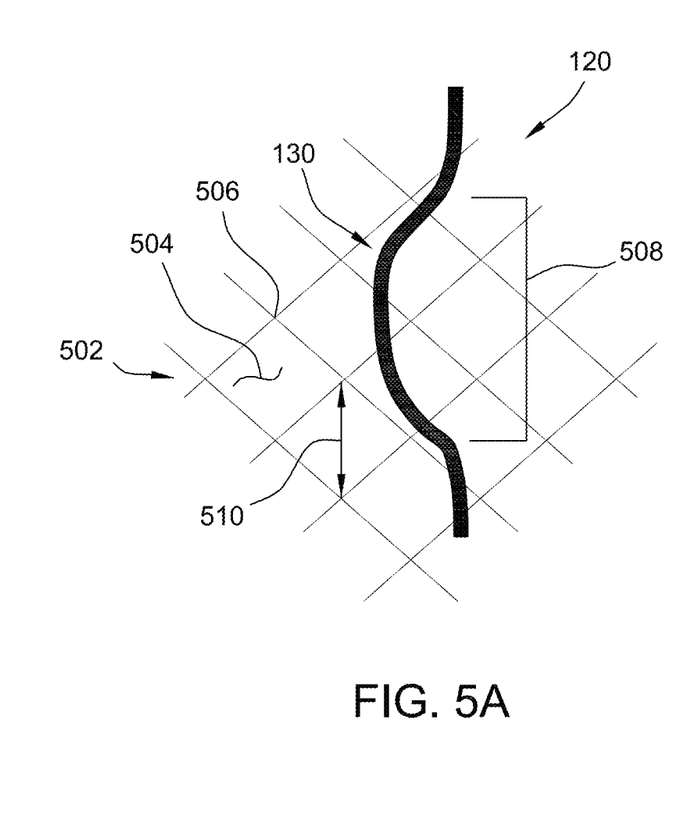
FIGS. 5A and 5B illustrate a first example embodiment of a stabilizing wire in accordance with the present disclosure.
Figure 5B:
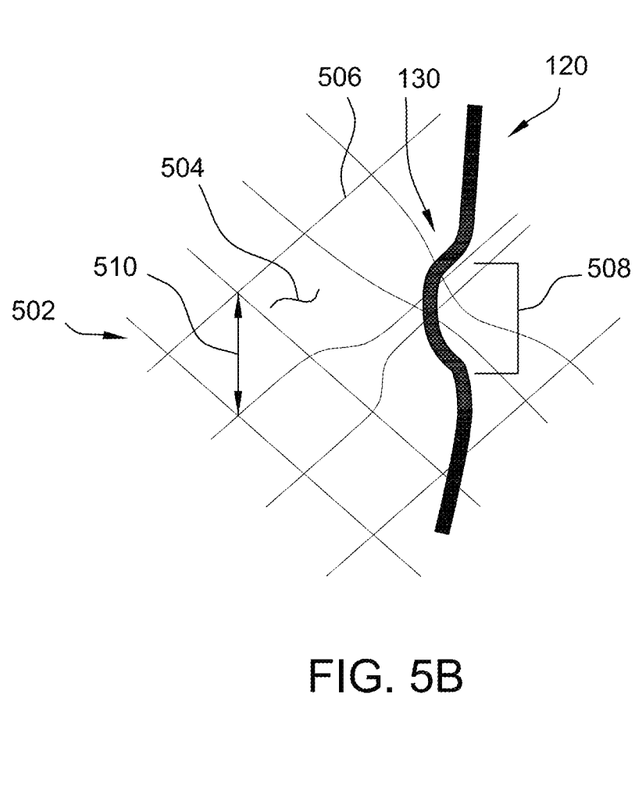
Figure 6A:
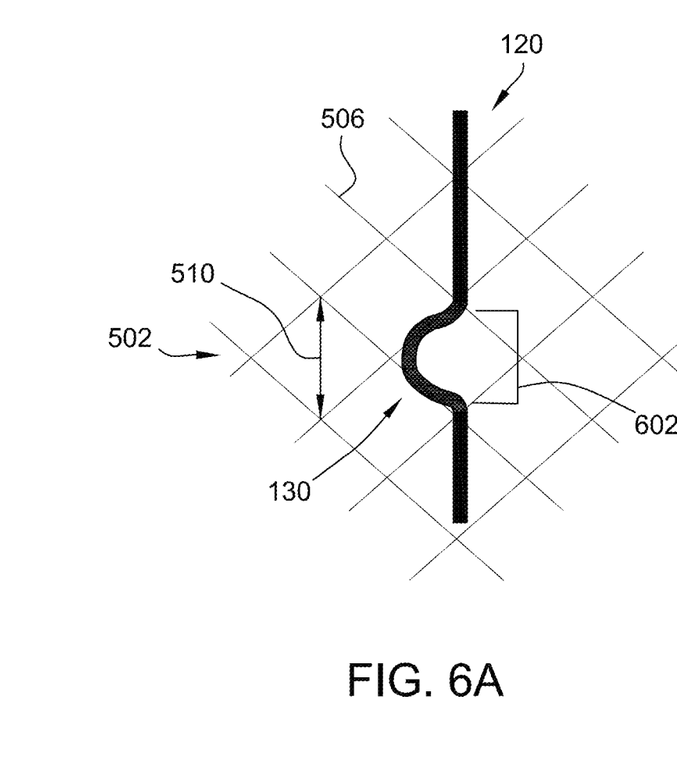
FIGS. 6A and 6B illustrate a second example embodiment of a stabilizing wire in accordance with the present disclosure.
Figure 6B:
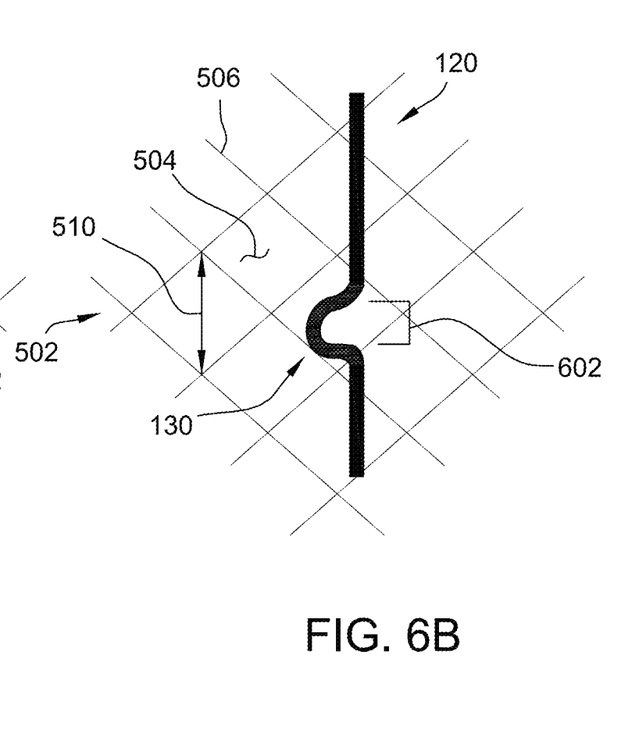

Turning now to FIGS. 5A and 5B, one embodiment of a stabilizing wire 120 is shown, and another embodiment of stabilizing wire 120 is shown in FIGS. 6A and 6B. FIGS. 5A and 6A each illustrate the respective embodiment of stabilizing wire 120 in the first position (e.g., deployed), and FIGS. 5B and 6B each illustrate the respective embodiment of stabilizing wire 120 in the second position (e.g., retracted). In this embodiment, device body 106 (e.g., lobe 114) is formed from a braided mesh material 502, which defines a plurality of cells 504 between wires 506 of material 502.

In the illustrated embodiment of FIGS. 5A and 5B, ramp segment 130 has a length 508 that is greater than a length 510 of a single cell 504 of material 502. When stabilizing wire 120 is transitioned to the second position, in some instances, ramp segment 130 may engage one or more wires 506 of material 502, which may cause material 502 to bunch. In some cases, this interaction with wires 506 of material 502 may interfere with retraction of stabilizing wire 120, such that stabilizing wire 120 may not fully transition to the second position.

Accordingly, in other embodiments, as shown in FIGS. 6A and 6B, ramp segment 130 may have a length 602 that is less than length 510 of cell 504 of material 502. In some such embodiments, ramp segment 130 may be less likely to engage wires 506 when stabilizing wire 120 is transitioned to the second position.

Figure 7:
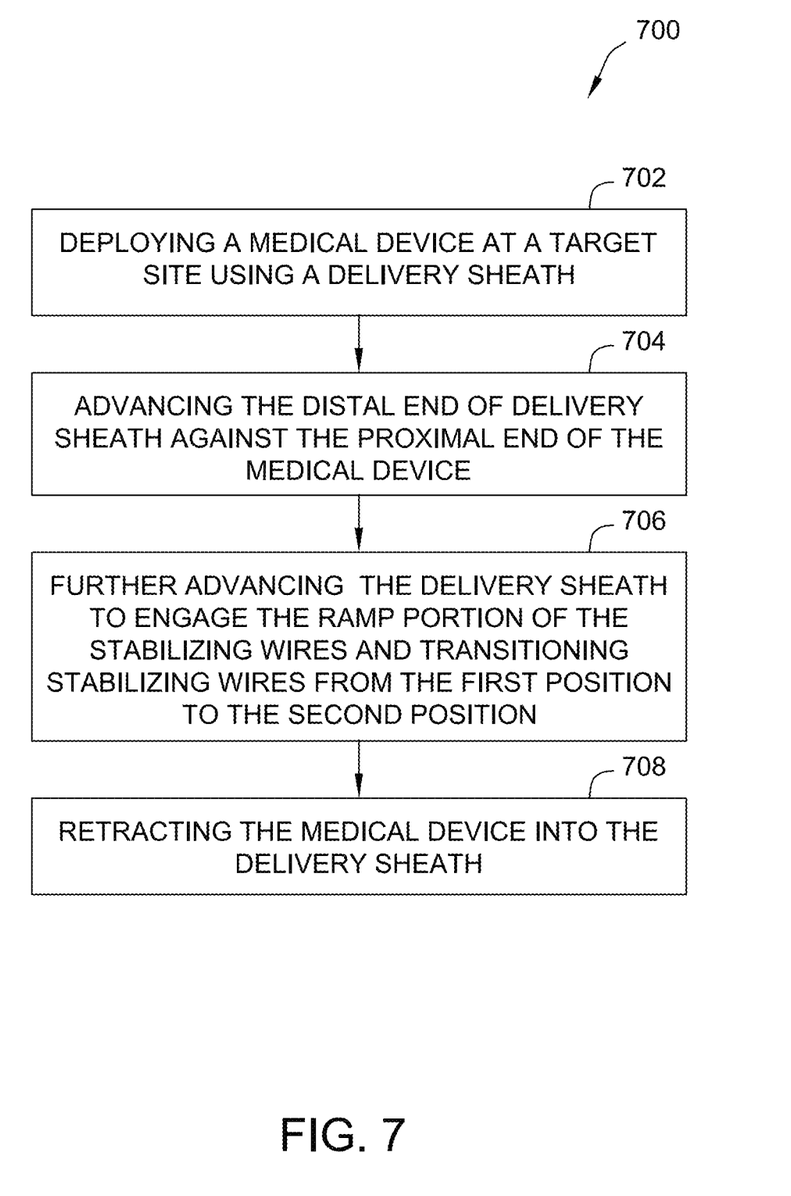
FIG. 7 is a flow diagram of a method of recapturing a medical device.

FIG. 7 is a flow diagram of a method 700 for recapturing a medical device (e.g., medical device 104) at a target site in a subject using a delivery sheath (e.g., delivery sheath 102, both shown in FIG. 2), according to one embodiment.

Method 700 includes deploying 702 the medical device at the target site using the delivery sheath. As described herein, the medical device includes a device body and a plurality of stabilizing wires coupled to the device body, each stabilizing wire having a respective proximal end and distal end and being selectively movable between a first position in which at least a portion of the distal end extends radially outwardly from the device body and a second position in which the distal end is retracted within the device body. Each stabilizing wire respectively includes: (i) a linear portion at least partially defining the proximal end, (ii) a hook portion at least partially defining the distal end, and (iii) a ramp segment extending between the linear portion and the hook portion, the ramp segment including a ramp incline portion that extends at a first angle away from the linear portion to a ramp apex, and a ramp decline portion that extends at a second angle from the hook portion to the ramp apex.

Method 700 also includes recapturing the medical device by: advancing 704 a distal end of the delivery sheath against a proximal end of the medical device, further advancing 706 the delivery sheath to engage the ramp portion of the stabilizing wires with the distal end of the delivery sheath and to transition the stabilizing wires from the first position to the second position, and retracting 708 the medical device into the delivery sheath.

Method 700 may include additional, alternative, and/or fewer steps, including those described herein. For example, in some embodiments, further advancing 706 includes rotating each stabilizing wire about the respective proximal end thereof to retract each stabilizing wire into the device body. In some embodiments, rotating each stabilizing wire about the respective proximal end to retract each stabilizing wire into the device body includes rotating each stabilizing wire about the respective proximal end thereof to move the respective hook portion thereof entirely into the device body.

While embodiments of the present invention have been described, it should be understood that various changes, adaptations and modifications may be made therein without departing from the spirit of the invention and the scope of the appended claims. For example, it is anticipated that the device body portion could be cylindrical, barrel shaped, concave, convex, tapered, or a combination of shapes without departing from the invention herein. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device comprising:
   a device body including at least one lobe formed from a shape memory material; and
   a plurality of stabilizing wires coupled to the device body, each stabilizing wire having a respective proximal end and distal end and being selectively movable between a first position in which at least a portion of the distal end extends radially outwardly from the device body and a second position in which the distal end is retracted within the device body, each stabilizing wire respectively comprising:
- a linear portion at least partially defining the proximal end;
- a hook portion at least partially defining the distal end; and
- a ramp segment extending between the linear portion and the hook portion, the ramp segment comprising a ramp incline portion that extends at a first angle away from the linear portion to a ramp apex, and a ramp decline portion that extends at a second angle from the hook portion to the ramp apex.

2. The medical device of claim 1, wherein the hook portion of the wire is positioned proximate to a distal end of the at least one lobe.

3. The medical device of claim 1, wherein each stabilizing wire is coupled to the at least one lobe at the respective proximal end of the stabilizing wire.

4. The medical device of claim 1, wherein the first angle between the ramp incline portion and the linear portion is between about 60° and about 80°.

5. The medical device of claim 1, wherein the second angle between the ramp decline portion and the hook portion is between about 60° and about 80°.

6. The medical device of claim 1, wherein the ramp apex is a curved transition between the ramp incline portion and the ramp decline portion.

7. The medical device of claim 1, wherein the shape memory material comprises a braided mesh fabric.

8. The medical device of claim 7, wherein the braided mesh fabric comprises a plurality of cells, wherein each ramp segment is adjacent to a respective cell of the plurality of cells, and wherein a length of each ramp segment is less than a length of the respective adjacent cell.

9. The medical device of claim 1, wherein each stabilizing wire is coupled to an exterior surface of the at least one lobe.

10. The medical device of claim 1, wherein the at least one lobe comprises an exterior surface that defines a cavity within the at least one lobe, wherein the respective distal end of each stabilizing wire is positioned within the cavity in the second position.

11. A delivery system comprising:
a medical device comprising:
- a device body including at least one lobe formed from a shape memory material; and
- a plurality of stabilizing wires coupled to the device body, each stabilizing wire having a respective proximal end and distal end and being selectively movable between a first position in which at least a portion of the distal end extends radially outwardly from the device body and a second position in which the distal end is retracted within the device body, each stabilizing wire respectively comprising:
  - a linear portion at least partially defining the proximal end;
  - a hook portion at least partially defining the distal end; and
  - a ramp segment extending between the linear portion and the hook portion, the ramp segment comprising a ramp incline portion that extends at a first angle away from the linear portion to a ramp apex, and a ramp decline portion that extends at a second angle from the hook portion to the ramp apex; and
a delivery sheath configured to retain and recapture the medical device during deployment of the medical device to a target site.

12. The delivery system of claim 11, wherein the device is back-loaded into the delivery sheath.

13. The delivery system of claim 11, wherein contact between the delivery sheath and the ramp segment as the medical device is retracted proximally into the delivery sheath transitions the plurality of stabilizing wires from the first position to the second position.

14. The delivery system of claim 13, wherein, as the medical device is retracted proximally into the delivery sheath, the delivery sheath is configured to engage the linear portion of the stabilizing wire and, subsequently, engage the ramp incline portion to initiate selectively moving the plurality of stabilizing wires from the first position to the second position.

15. The delivery system of claim 11, wherein the delivery sheath is configured to fully recapture the medical device when the plurality of stabilizing wires are in the second position.

16. The delivery system of claim 11, wherein the first angle between the ramp incline portion and the linear portion is between about 600 and about 800, and wherein the second angle between the ramp decline portion and the hook portion is between about 600 and about 800.

17. The delivery system of claim 11, wherein the at least one lobe comprises an exterior surface that defines a cavity within the at least one lobe, wherein the respective distal end of each stabilizing wire is positioned within the cavity in the second position.

18. A method of recapture of the medical device comprising:
deploying a medical device at a target site using a delivery sheath, the medical device including a device body and a plurality of stabilizing wires coupled to the device body, each stabilizing wire having a respective proximal end and distal end and being selectively movable between a first position in which at least a portion of the distal end extends radially outwardly from the device body and a second position in which the distal end is retracted within the device body, each stabilizing wire respectively including: (i) a linear portion at least partially defining the proximal end, (ii) a hook portion at least partially defining the distal end, and (iii) a ramp segment extending between the linear portion and the hook portion, the ramp segment including a ramp incline portion that extends at a first angle away from the linear portion to a ramp apex, and a ramp decline portion that extends at a second angle from the hook portion to the ramp apex; and
recapturing the medical device by:
- advancing a distal end of the delivery sheath against a proximal end of the medical device;
- further advancing the delivery sheath to engage the ramp portion of the stabilizing wires with the distal end of the delivery sheath and to transition the stabilizing wires from the first position to the second position; and
- retracting the medical device into the delivery sheath.

19. The method of claim 18, wherein further advancing the delivery sheath to engage the ramp portion of the stabilizing wires comprises rotating each stabilizing wire about the respective proximal end thereof to retract each stabilizing wire into the device body.

20. The method of claim 19, wherein rotating each stabilizing wire about the respective proximal end to retract each stabilizing wire into the device body comprises rotating each stabilizing wire about the respective proximal end thereof to move the respective hook portion thereof entirely into the device body.

\* \* \* \* \*